(12) United States Patent
Bonda et al.

(10) Patent No.: US 7,597,825 B2
(45) Date of Patent: *Oct. 6, 2009

(54) METHOD OF QUENCHING ELECTRONIC EXCITATION OF CHROMOPHORE-CONTAINING ORGANIC MOLECULES IN PHOTOACTIVE COMPOSITIONS

(75) Inventors: Craig A. Bonda, Winfield, IL (US); Anna Pavlovic, Elmwood Park, IL (US)

(73) Assignee: Hallstar Innovations Corp., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/891,281

(22) Filed: Aug. 9, 2007

(65) Prior Publication Data

US 2009/0039323 A1    Feb. 12, 2009

(51) Int. Cl.
*F21V 9/04* (2006.01)
*F21V 9/06* (2006.01)
*G02B 5/22* (2006.01)
*G02B 5/26* (2006.01)

(52) U.S. Cl. .......................... 252/589; 424/59; 424/60; 424/401; 514/520; 524/90; 558/410

(58) Field of Classification Search ............... 524/90; 424/59, 60; 514/520; 252/589
See application file for complete search history.

(56) References Cited

U.S. PATENT DOCUMENTS

| | | | |
|---|---|---|---|
| 2,623,060 A | 12/1952 | Cragoe | |
| 3,215,724 A | 11/1965 | Strobel et al. | |
| 3,337,357 A | 8/1967 | Strobel et al. | |
| 4,284,621 A | 8/1981 | Preuss et al. | |
| 4,307,240 A | 12/1981 | Ching | |
| 4,562,278 A | 12/1985 | Hill | |
| 5,576,354 A | 11/1996 | Deflandre et al. | |
| 5,738,842 A * | 4/1998 | Raspanti et al. | 424/59 |
| 5,783,307 A * | 7/1998 | Fagerburg et al. | 428/412 |
| 5,989,528 A | 11/1999 | Tanner et al. | |
| 6,113,931 A | 9/2000 | Bonda et al. | |
| 6,284,916 B1 | 9/2001 | Bonda et al. | |

(Continued)

FOREIGN PATENT DOCUMENTS

DE    1222926    8/1966

(Continued)

OTHER PUBLICATIONS

Katritzky, Alan R.; Nair, Satheesh K.; Witek, Rachel M.; Hutchins, Steven M. Synthesis of 3,3-diarylpyrrolidines from diaryl ketones, ARKIVOC (Gainesville, FL, United States) (2003), (5),pp. 9-18 Arkat USA Inc. URL: http://www.arkatusa.org/zark/journal/2003/Bernath/GB-594J/594J.pdf.*

(Continued)

*Primary Examiner*—Ling-Siu Choi
*Assistant Examiner*—Bijan Ahvazi
(74) *Attorney, Agent, or Firm*—Marshall, Gerstein & Borun LLP

(57) ABSTRACT

The photostabilizing electronic excited state energy—particularly singlet state energy from a UV-absorbing molecule has been found to be readily transferred to (accepted by) α-cyanodiphenylacrylate compounds of formulas (I) and (V) having an alkoxy radical preferably in the four (para) position (hereinafter methoxy crylenes) on one or both of the phenyl rings:

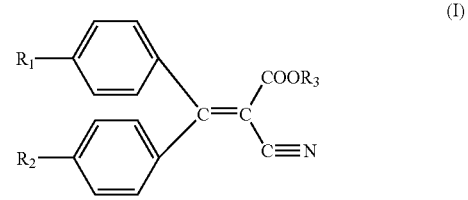

(I)

wherein at least one of $R_1$ and $R_2$ is a straight or branched chain $C_1$-$C_{12}$ alkoxy radical, preferably $C_1$-$C_8$, more preferably $C_1$-$C_4$, and most preferably methoxy, and any non-alkoxy radical $R_1$ or $R_2$ is hydrogen; and $R_3$ is a straight or branched chain $C_1$-$C_{24}$ alkyl radical, preferably $C_{12}$-$C_{24}$, more preferably $C_{20}$;

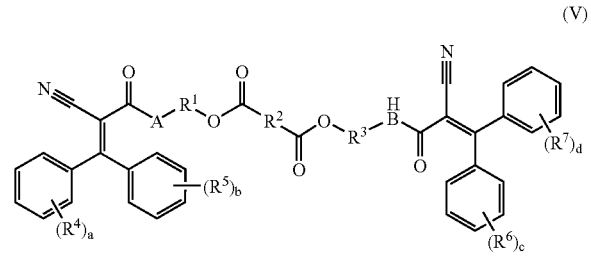

(V)

wherein A and B are the same or different and are selected from the group consisting of oxygen, amino and sulfur; $R^1$ and $R^3$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$ is selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_1$-$C_{30}$ substituted alkylene, $C_2$-$C_{30}$ substituted alkyne; $R^4$, $R^5$, $R^6$ and $R^7$ are the same or different and are selected from the group consisting of $C_1$-$C_{30}$ alkoxy straight chain or branched and a, b, c and d are each either 0 or 1, and a, b, c and d add up to 1, 2, 3, or 4.

19 Claims, 4 Drawing Sheets

U.S. PATENT DOCUMENTS

| | | |
|---|---|---|
| 6,485,713 B1 | 11/2002 | Bonda et al. |
| 6,518,451 B2 | 2/2003 | Bonda et al. |
| 6,537,529 B1 | 3/2003 | Bonda |
| 6,551,605 B2 | 4/2003 | Bonda |
| 6,800,274 B2 | 10/2004 | Bonda et al. |
| 6,919,473 B2 | 7/2005 | Bonda et al. |
| 6,962,692 B2 | 11/2005 | Bonda et al. |
| 7,235,587 B2 | 6/2007 | Bonda et al. |
| 2003/0000130 A1* | 1/2003 | Wood et al. .................. 44/275 |
| 2003/0176542 A1* | 9/2003 | Abe et al. .................... 524/91 |
| 2004/0047817 A1* | 3/2004 | Bonda ......................... 424/59 |
| 2004/0047818 A1 | 3/2004 | Bonda |
| 2004/0247539 A1 | 12/2004 | Wendel et al. |
| 2005/0191249 A1 | 9/2005 | Bonda et al. |
| 2006/0002869 A1 | 1/2006 | Bonda et al. |

FOREIGN PATENT DOCUMENTS

| | | |
|---|---|---|
| EP | 1323743 | 7/2003 |
| JP | 2005139263 | 6/2005 |
| SU | 1273360 | 11/1986 |
| WO | WO-0027337 | 5/2000 |
| WO | WO-0242368 | 5/2002 |

OTHER PUBLICATIONS

Eric Chatelain and Bernard Gabard, Photostabilization of Butyl methoxydibenzoylmethane (Avobenzone) and Ethylhexyl methoxycinnamate by Bis-ethylhexyloxyphenol methoxyphenyl triazine (Tinosorb S), a New UV Broadband Filter, Photochemistry and Photobiology, 2001, 74(3): 401-406.*

Craig Bonda, Research Pathways to Photostable Sunscreens, Feb. 5, 2008, vol. 123, No. 2. pp. 1, 49-60. issue of Cosmetics & Toiletries Magazine.*

European Search Report for EP 08 10 3204, dated Jul. 17, 2008.

European Search Report for EP 08 10 3205, dated Jul. 25, 2008.

N. G. Senchenya, et al., *Silicon-containing esters of α-cyanoacrylic acid: synthesis and properties*, Russian Chemical Bulletin, vol. 42, No. 5, May 1993, pp. 909-911.

International Search Report for PCT/US2008/058456 dated Jun. 27, 2008.

Written Opinion for PCT/US2008/058456 dated Jun. 27, 2008.

* cited by examiner

METHOD OF QUENCHING ELECTRONIC EXCITATION OF CHROMOPHORE-CONTAINING ORGANIC MOLECULES IN PHOTOACTIVE COMPOSITIONS

FIELD OF THE INVENTION

The present invention is directed to a method of quenching electronic excited e(s) of chromophore-containing UV-absorbing organic molecules in photoactive compositions. More particularly, it has been found that α-cyano-β,β diphenylacrylates (crylenes) having an alkoxy radical, preferably on one of the phenyl rings (alternatively on both phenyl rings), quenches the excited state of the chromophore by accepting the excited state energy (singlet and sometimes also the triplet state), thereby returning the UV-absorbing molecule back to its ground state so that the chromophore can absorb more photons, e.g., from ultraviolet (UV) light, thereby photostabilizing UV-absorbing chromophore-containing organic molecules, particularly butyl methoxydibenzoylmethane (Avobenzone), octyl methoxycinnamate (Octinoxate), and octyl salicylate (Octisalate) in photoactive compositions.

BACKGROUND

The absorption of ultraviolet light by a chromophore-containing organic molecule causes the excitation of an electron in the chromophore moiety from an initially occupied, low energy orbital to a higher energy, previously unoccupied orbital. The energy of the absorbed photon is used to energize an electron and cause it to "jump" to a higher energy orbital, see Turro, Modern Molecular Photochemistry, 1991. Two excited electronic states derive from the electronic orbital configuration produced by UV light absorption. In one state, the electron spins are paired (antiparallel) and in the other state the electron spins are unpaired (parallel). The state with paired spins has no resultant spin magnetic moment, but the state with unpaired spins possesses a net spin magnetic moment. A state with paired spins remains a single state in the presence of a magnetic field, and is termed a singlet state. A state with unpaired spins interacts with a magnetic field and splits into three quantized states, and is termed a triplet state.

In the electronically excited state, the chromophore-containing organic molecule is prone to degrade via a number of known pathways and, therefore, can absorb little or no additional UV light. To photostabilize an electronically excited chromophore-containing organic molecule in order to provide sufficient UV protection, it must be returned to the ground state before it undergoes a photochemical reaction destructive to its UV absorbing capability. There are known photostabilizing sunscreen additives, such as Octocrylene, methylbenzilydene camphor, and the esters or polyesters of naphthalene dicarboxylic acid of this assignee's U.S. Pat. Nos. 6,113,931; 6,284,916; 6,518,451; and 6,551,605, all hereby incorporated by reference, that are capable of quenching excited triplet state energy. Surprisingly, it has been found that alkoxy crylenes, particularly methoxy crylenes, return chromophore-containing organic molecules, particularly butyl methoxydibenzoylmethane (Avobenzone), octyl methoxycinnamate (Octinoxate), and octyl salicylate (Octisalate), from both an electronically excited singlet state and excited triplet state back to their ground state, thereby photostabilizing the UV-absorbing organic molecules.

Deflandre U.S. Pat. No. 5,576,354 generally discloses a cosmetic sunscreen composition containing at least 1% by weight of an α-cyano-β,β-diphenylacrylate that will photostabilize a dibenzoylmethane derivative, e.g., Parsol 1789 (Avobenzone), so long as the composition contains a fatty phase, e.g., glycerol stearates, isopropyl myristate or the like, and so long as the mole ratio of the α-cyano-β,β-diphenylacrylate to the dibenzoylmethane derivative is at least 0.8. The compounds preferred in the '354 patent and disclosed in the examples are octocrylene, which contains no alkoxy radical(s) (UVINULN 539); β,β-bis (4-methoxyphenyl)acrylates (containing no cyano radical); and the α-cyano-β,β-diphenylacrylates, which contain no alkoxy radical(s).

As stated in this assignees pending applications, Ser Nos. 10/241,388; 10/361,223; and 10/786,793, an α-cyano-β,β-diphenylacrylate compound (e.g., octocrylene) is known to quench (accept) the excited triplet state energy of an excited photoactive compound by dissipating the energy kinetically in the form of rapid isomerizations. This process is shown below:

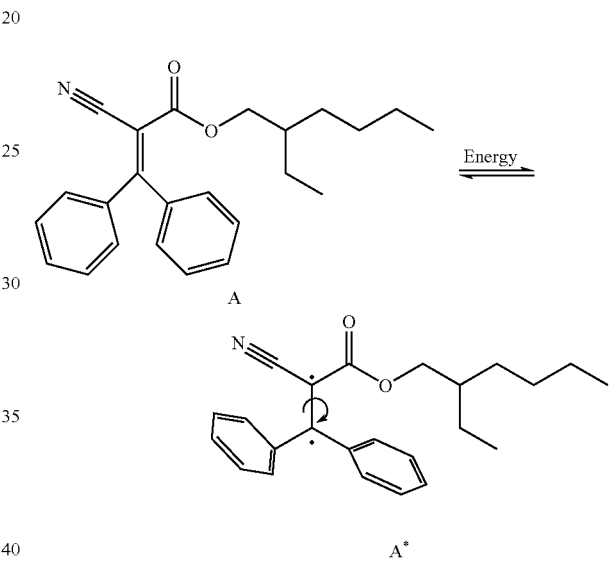

wherein the α-cyano-β,β-diphenylacrylate compound (octocrylene shown above as structure A), accepts the triplet excited state energy from a photoactive compound and forms a diradical (shown above as structure A*) at the α and β positions of the acrylate, which converts the double bond into a single bond and allows for the free rotation of the phenyl groups. This rotation occurs rapidly and efficiently to dissipate any excited triplet state energy accepted by the α-cyano-β,β-diphenylacrylate compound from the photoactive compound.

While octocrylene is able to quench (accept) the triplet excited state energy from a photoactive compound, thereby photostabilizing, to some degree, dibenzoylmethane derivatives, as shown in examples 1, 4, 6 and 8 of Deflandre et al. U.S. Pat. No. 5,576,354, hereby incorporated by reference, there exists a need in the photoactive composition art to find one or more compounds that quench (accept) the singlet excited state energy and preferably also the triplet excited state energy from photoactive compounds, which octocrylene does not.

Quite surprisingly, it has been found that the alkoxy substituted α-cyano-β,β-diphenylacrylates (alkoxy crylenes) will quench the electronically excited singlet state energy of UV-absorbing organic molecules, such as the dibenzoylmethane derivatives of U.S. Pat. No. 5,576,354, even at very low loadings compared to the quantity of UV-absorbing compounds.

SUMMARY

The photostabilizing electronic excited state energy—particularly singlet state energy from a UV-absorbing molecule—has been found to be readily transferred to (accepted by) α-cyanodiphenylacrylate compounds having an alkoxy radical in the four (Para) position (hereinafter methoxy crylenes) on one or both of the phenyl rings having the formula (I):

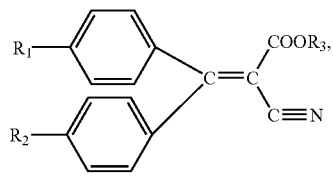

wherein one or both of $R_1$ and $R_2$ is a straight or branched chain $C_1$-$C_{30}$ alkoxy radical, preferably $C_1$-$C_8$, more preferably methoxy, and any non-alkoxy radical $R_1$ or $R_2$ is hydrogen; and $R_3$ is a straight or branched chain $C_1$-$C_{30}$ alkyl radical, preferably $C_2$-$C_{20}$.

DETAILED DESCRIPTION OF THE PREFERRED EMBODIMENTS

Figure 1:
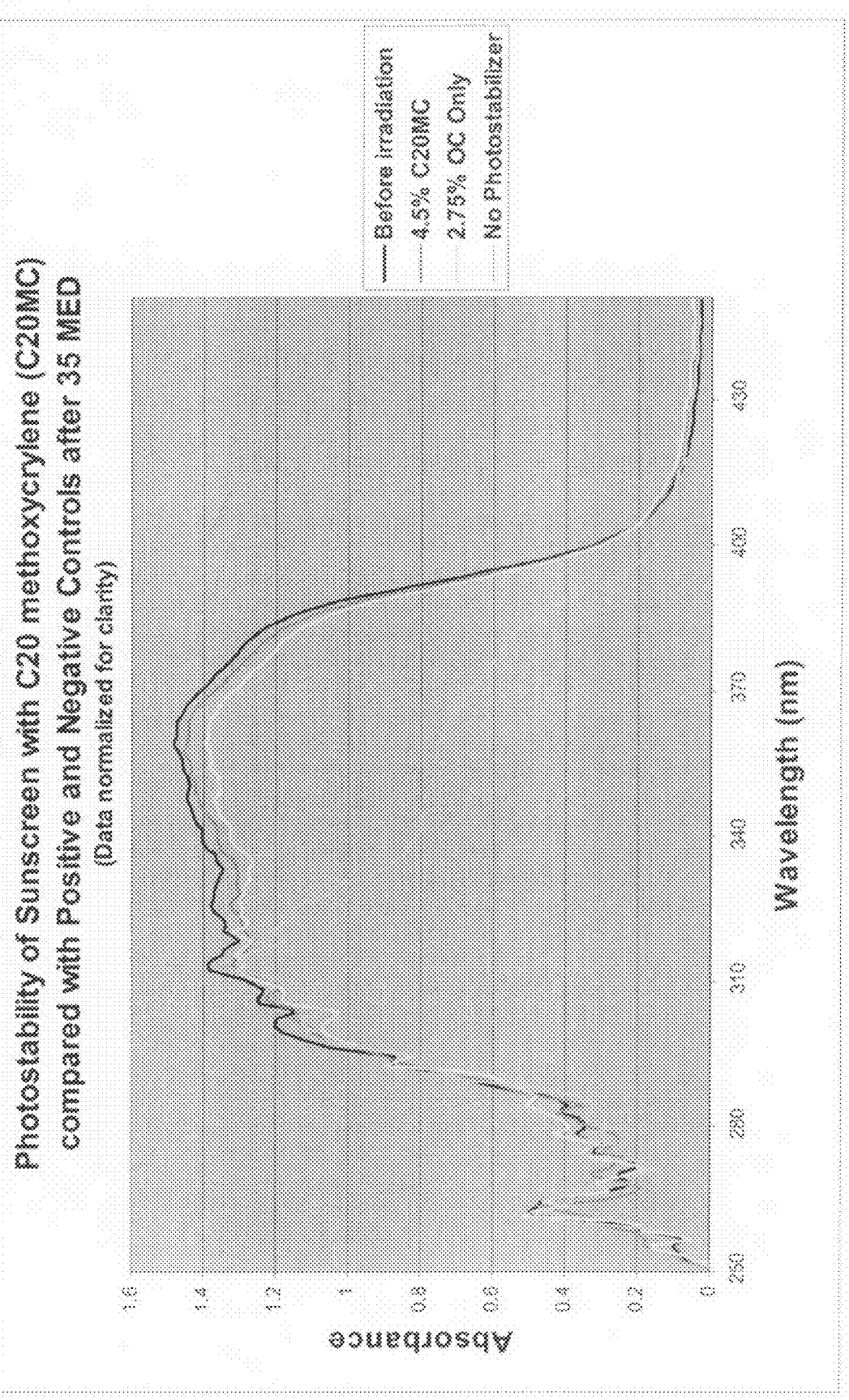
FIG. 1 is a graph showing the photostability of the sunscreen compositions of Examples 1-3 (when irradiated with 35 MED of UV radiation) provided by 4.5% octyldocedyl methoxy crylene (C2OMC); and 2.75% Octocrylene (OC) compared to the photostability prior to UV irradiation and compared to the composition with no photostabilizer.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "alkoxy" herein refers to a radical extending from the para position of one or both of the phenyl rings having the formula O—R, wherein R is an alkyl radical, straight chain or branched having 1 to 30 carbon atoms, preferably wherein R=$C_1$ to $C_8$, more preferably $C_2$-$C_{20}$, and most preferably —O—$CH_3$ (methoxy). The oxygen atom of the alkoxy radical is covalently bonded to the para carbon atom of one or both of the phenyl rings, preferably only one of the phenyls, preferably having the formula (II) or (III):

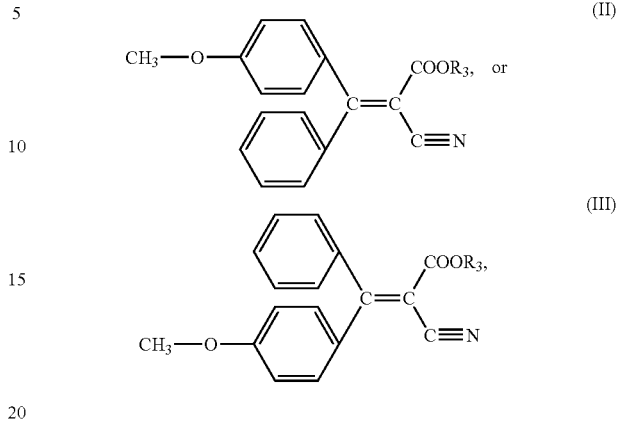

wherein $R_3$ is as previously defined.

The term "crylene" as used herein refers to a chromophoric moiety that includes an α-cyano-β,β-diphenyl propanoic acid ester.

The term "cyano" as used herein refers to a –C≡N group, also designated "—CN."

Photoactive compositions, e.g., sunscreen compositions, generally include UV-A and UV-B photoactive compounds in a cosmetically acceptable carrier, optionally including additives, such as emollients, stabilizers, emulsifiers, and combinations thereof. These additives can be used in preparing a UV filter composition in an emulsion (oil-in-water or water-in-oil) from a composition that includes one or more photoactive compounds and a solvent or a solvent combination that includes one or more organic solvents and water. When made, preferably the emulsion is an oil-in-water emulsion, wherein the oil phase is primarily formed from a mixture of the UV filter compound(s) and one or more organic solvents.

A typical photoactive composition includes one or more photoactive compounds, wherein the photoactive compound(s) act to absorb UV radiation and thereby protect the substrate (e.g., human skin, resins, films, and the like) from the harmful effects of UV radiation. The absorption process causes a photoactive compound to reach an excited state, wherein the excited state is characterized by the presence of excited electronic energy (e.g., singlet state energy or triplet state energy), as compared to the ground state of the photoactive compound. Once a photoactive compound reaches an excited state there exists a number of pathways by which the excited photoactive compound can dissipate its excess energy (e.g., singlet and/or triplet energy), however, many of those pathways adversely affect the ability of the photoactive compound to further absorb UV radiation. The alkoxy crylene molecules described herein accept electronic singlet excited state energy from UV-absorbers, particularly Avobenzone, octyl methoxycinnamate (Octinoxate), and octyl salicylate (Octisalate). The alkoxy crylenes also are very effective UVA absorbers in addition to providing electronic singlet state energy quenching of other UV-absorbing compounds in sunscreen compositions. The alkoxy crylene molecules described herein are especially effective when combined with one or more additional electronic singlet excited state quenching compounds such as oxybenzone. Particularly surprising photostabilization is achieved in sunscreen compositions containing the alkoxy crylene molecules described herein together with octyl methoxycinnamate and Avobenzone. The molar ratio of a compound of formula (I) to the photoactive compound can be less than 0.8, particularly about 0.1 to about 0.6.

A photoactive compound is one that responds to light photoelectrically. In the compositions and methods of photostabilization disclosed herein, a photoactive compound is one that responds to UV radiation photoelectrically. For example, all photoactive compound-containing compositions that respond to UV radiation photoelectrically by photoactive compound photodegradation benefit highly by the inclusion of the alkoxy crylene molecules described herein. The alkoxy crylenes described herein are useful photostabilizers and/or photoactive compounds when combined with any single or combination photoactive compounds identified in Shaath, Nadim, Encyclopedia of UV filters, © 2007, hereby incorporated by reference. Photostability is a problem with all UV filters because they all reach an electronic singlet excited state upon exposure to UV radiation.

It is theorized that the following UV filters are photostabilized by the alkoxy crylene molecules described herein, including all of the following, including combinations of any two or more, and include compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3 benzylidene, 4 methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, octabenzone, 4-isopropyldibenzoylmethane, butylmethoxydibenzoylmethane, etocrylene, and 4-isopropyl-dibenzoylmethane).

The following UV filters should be particularly photostabilized by the alkoxy crylene molecules described herein: 2-ethylhexyl p-methoxycinnamate, 4,4'-t-butyl methoxy-dibenzoylmethane, octyldimethyl p-aminobenzoate, digalloyltrioleate, ethyl 4-[bis(hydroxypropyl)]aminobenzoate, 2-ethylhexylsalicylate, glycerol p-aminobenzoate, 3,3,5-trimethylcyclohexylsalicylate, and combinations thereof.

Photoactive compositions disclosed herein can include a variety of photoactive compounds, preferably including one or more UV-A photoactive compounds and one or more UV-B photoactive compounds. Preferably, a sunscreen composition includes a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; uric acid derivatives; vilouric acid derivatives; tannic acid and derivatives thereof; hydroquinone; diethylamino hydroxybenzoyl hexyl benzoate and salts and derivatives thereof; and combinations of the foregoing.

UV A radiation (about 320 nm to about 400 nm), is recognized as contributing to causing damage to skin, particularly to very lightly colored or sensitive skin. A sunscreen composition disclosed herein preferably includes a UV-A photoactive compound. Preferably, a sunscreen composition disclosed herein includes a dibenzoylmethane derivative UV-A photoactive compound. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

For a product marketed in the United States, preferred cosmetically acceptable photoactive compounds and concentrations (reported as a percentage by weight of the total cosmetic sunscreen composition) include: aminobenzoic acid (also called para aminobenzoic acid and PABA; 15% or less), Avobenzone (also called butyl methoxy dibenzoylmethane; 3% or less), cinoxate (also called 2 ethoxyethyl p methoxycinnamate; 3% or less), dioxybenzone (also called benzophenone 8; 3% or less), homosalate ((also called 3,3,5-trimethylcyclohexyl salicylate, 15% or less), menthyl anthranilate (also called menthyl 2 aminobenzoate; 5% or less), octocrylene (also called 2 ethylhexyl 2 cyano 3,3 diphenylacrylate; 10% or less), octyl methoxycinnamate (7.5% or less), octyl salicylate (also called 2 ethylhexyl salicylate; 5% or less), oxybenzone (also called benzophenone 3; 6% or less), padimate O (also called octyl dimethyl PABA; 8% or less), phenylbenzimidazole sulfonic acid (water soluble; 4% or less), sulisobenzone (also called benzophenone 4; 10% or less), titanium dioxide (25% or less), trolamine salicylate (also called triethanolamine salicylate; 12% or less), and zinc oxide (25% or less).

Other preferred cosmetically acceptable photoactive compounds and preferred concentrations (percent by weight of the total cosmetic sunscreen composition) include diethanolamine methoxycinnamate (10% or less), ethyl-bis(hydroxypropyl) aminobenzoate (5% or less), glyceryl aminobenzoate (3% or less), 4 isopropyl dibenzoylmethane (5% or less), 4 methylbenzylidene camphor (6% or less), terephthalylidene dicamphor sulfonic acid (10% or less), and sulisobenzone (also called benzophenone 4, 10% or less).

For a product marketed in the European Union, preferred cosmetically acceptable photoactive compounds and preferred concentrations (reported as a percentage by weight of the total cosmetic sunscreen composition) include: PABA (5% or less), camphor benzalkonium methosulfate (6% or less), homosalate (10% or less), benzophenone 3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG 25 PABA (10% or less), isoamyl p methoxycinnamate (10% or less), ethylhexyl triazone (5% or less), drometrizole trielloxane (15% or less), diethylhexyl butamido triazone (10% or less), 4 methylbenzylidene camphor (4% or less), 3 benzylidene camphor (2% or less), ethylhexyl salicylate (5% or less), ethylhexyl dimethyl PABA (8% or less), benzophenone 4 (5%, expressed as acid), methylene bis benztriazolyl tetramethylbutylphenol (10% or less), disodium phenyl dibenzimidazole tetrasulfonate (10% or less, expressed as acid), bis ethylhexyloxyphenol methoxyphenol triazine (10% or less), methylene bisbenzotriazolyl tetramethylbutylphenol (10% or less, also called TINOSORB M or Bisoctrizole), and bisethylhexyloxyphenol methoxyphenyl triazine.(10% or less, also called TINOSORB S or Bemotrizinol).

All of the above described UV filters are commercially available. For example, suitable commercially available organic UV filters are identified by trade name and supplier in Table I below:

TABLE I

| CTFA Name | Trade Name | Supplier |
|---|---|---|
| benzophenone-3 | UVINUL M-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| diethylamino hydroxybenzoyl hexyl benzoate | UVINUL A-PLUS | BASF Chemical Co. |
| diethylhexyl butamido triazone | UVISORB HEB | 3V-Sigma |
| disodium phenyl dibenzylimidazole | NEO HELIOPAN AP | Symrise |
| ethyl dihydroxypropyl-PABA | AMERSCREEN P | Amerchol Corp. |
| glyceryl PABA | NIPA G.M.P.A. | Nipa Labs. |
| homosalate | KEMESTER HMS | Humko Chemical |
| menthyl anthranilate | SUNAROME UVA | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)-camphor | EUSOLEX 6300 | EM Industries |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 | Givaudan Corp. |
| etocrylene | UVINUL N-35 | BASF Chemical Co. |
| methylene bisbenzotriazolyl tetramethylbutylphenol | TINOSORB M | Ciba Specialty Chemicals |
| bisethylhexyloxyphenol methoxyphenyl triazine. | TINOSORB S | Ciba Specialty Chemicals |

Commonly-assigned U.S. Pat. Nos. 6,485,713 and 6,537,529, the disclosures of which are hereby incorporated herein by reference, describe compositions and methods for increasing the photostability of photoactive compounds in a sunscreen composition, e.g., by the addition of polar solvents to the oil phase of a composition. By increasing the polarity of the oil phase of a sunscreen composition including the alkoxy crylenes described herein, e.g., methoxy crylene, the stability of the sunscreen composition is surprisingly increased in comparison to octocrylene. In the sunscreen compositions described herein, preferably, one or more of a highly polar solvent is present in the oil-phase of the composition. Preferably, a sufficient amount of a polar solvent is present in the sunscreen composition to raise the dielectric constant of the oil-phase of the composition to a dielectric constant of at least about 7, preferably at least about 8. With or without the highly polar solvent in the oil phase, the methoxy crylene molecules described herein yield unexpected photostability in comparison to octocrylene.

A photoactive compound can be considered stable when, for example, after 30 MED irradiation the photoactive compound has retained at least about 90% of its original absorbance at a wavelength, or over a range of wavelengths of interest (e.g., the wavelength at which a photoactive compound has a peak absorbance, such as 350-370 nm for Avobenzone). Likewise, a sunscreen composition can include a plurality of photoactive compounds and a sunscreen composition, as a whole, can be considered stable when, for example, after 30 MED irradiation the sunscreen composition has retained at least about 90% of its original absorbance at one or more wavelengths of interest (e.g., at or near the peak absorbance wavelength of the primary photoactive compound).

Synthesis of methyl or ethyl 2-cyano-3-(4'-methoxyphenyl)-3-phenylpropenoate (Methyl or Ethyl Methoxycrylene or Methyl or Ethyl MeOcrylene)

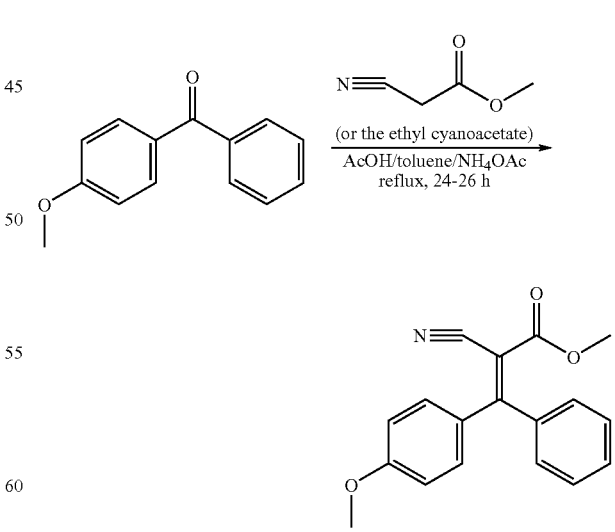

4-Methoxy benzophenone (MW=182.22 g/mole; 500 g; 2.74 mole; 1 mole equivalence) and methyl cyanoacetate (MW=99.09 g/mole; 367.06 g; 3.70 mole; 1.35 mole equivalence) were placed in 1-L 3-neck flask assembled with mechanical stirrer and nitrogen inlet, which provided continuous flow of nitrogen through the reaction mixture (nitrogen is bubbled through the reaction mixture). Next, toluene (1200 ml) and acetic acid (240 ml; ratio of toluene/acetic acid=5/1) are added to the flask followed by ammonium acetate (MW=77.09 g/mole; 21.12 g; 0.274 mole, 0.1 mole equivalence; the catalyst is added 4 times this amount during reaction time). The flask is then assembled with Dean-Stark receiver through which reaction water is being continuously removed.

Comments:

1. Aliquots of the reaction mixture are taken to check the rate of completion of the reaction.
2. The amount of water expected from this reaction is 49.5 ml. However, I collected about 120 ml of water phase. This is due to the fact that the water is distilled in form of a mixture, water/acetic acid/toluene.
3. To prevent from loosing the methyl acetate from the reaction mixture, it helps to put a short packed column between Dean-Stark receiver and the flask.

Work-up:

The reaction mixture is cooled to room temperature and ethyl acetate is added to dissolve all solids before the crude mixture is washed several time with water, to remove acetic acid and salts. The solvents are then removed from the reaction mixture by distillation. The crude solid product is re-crystallized from hot methanol (or toluene/methanol mixture, if such is preferred).

Comments:

The finished product begins to crystallize out from the cooling reaction mixture and thus can be filtered off, but it still is very acidic, so the crystals ought to be washed with water/methanol mixture to wash out any acetic acid and salts residues. Thus obtained the product then can be re-crystallized and the mother liquor can be washed with water, dried, and second crop of the product can be obtained.

Synthesis of Alkyl 2-cyano-3-(4'-methoxyphenyl)-3-phenylpropenoate

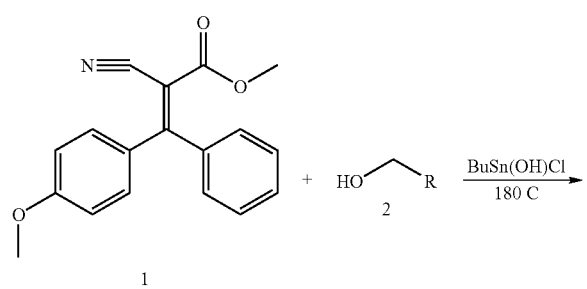

-continued

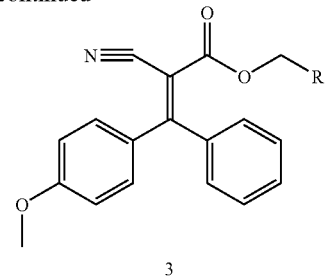

Reaction Procedure:

Methyl (or ethyl) 2-cyano-3-(4'-methoxyphenyl)-3-phenylpropenoate (900 g, 3.06 mole; MW=293.32), alkyl alcohol (3.84 mole; 1.25 mole equivalence), and Tegokat 250 (0.03% of total batch weight) were placed in 2 L 3-neck round-bottom flask and heated to temperature set at 185 C (365 F), with nitrogen purging it well to remove forming methanol (or ethanol) via the simple distillation setup with packed column. After 3 h, GC showed full conversion of methyl 2-cyano-3-(4'-methoxyphenyl)-3-phenylpropenoate to the desired product.

Work-up:

The unreacted alkyl alcohol was completely removed by vacuum distillation. Temperature of the reaction was lowered to 110 C (230 F) and calculated amount (2% of total batch weight) of the SSP (tin removing agent) was added. The product was stirred at this temperature for 2 hours and then filtered hot. Small amount of celite was added right before filtration to enhance the filtration—with celite the filtration was more efficient and faster.

Results:

| Yield of the product | 94% of stoichiometric amount |
| Purity of finished product | 99.81% (area count, GC). |

EXAMPLES

The following compositions (Table I) were prepared according to the procedure indicated in order to show the photostability effect of the alkoxy crylenes described herein. The compound described as "methoxy crylene" had the following formula (IV):

(IV)

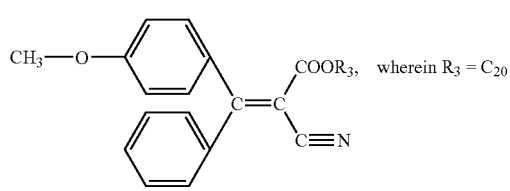

| | | COMPOSITIONS OF FORMULATIONS TESTED FOR PHOTOSTABILITY | | |
|---|---|---|---|---|
| | | | **Reported as Coefficients of Variation on report generated by Labsphere instrument | |
| # | Ingredients | CAB6-043 (4.5% C20 Methoxycrylene) | CAB6-044 (POS: 2.75% OC Only) | CAB6-046 (NEG: No Photostabilizer) |
| | Oil Phase ingredients | | | |
| 1 | Avobenzone | 3.00% | 3.00% | 3.00% |
| 2 | Octisalate | 5.00% | 5.00% | 5.00% |
| 3 | Homosalate | 7.50% | 7.50% | 7.50% |
| 4 | Benzophenone-3 | 0.49% | 0.49% | 0.49% |
| 5 | Octocrylene*** (OC) | 0.00% | 2.75% | 0.00% |
| 6 | C20 Methoxycrylene*** (C20MC) | 4.50% | 0.00% | 0.00% |
| 7 | Phenylethyl benzoate | 0.00% | 0.00% | 2.75% |
| 8 | Dimethicone (350 cSt) | 1.25% | 1.25% | 1.25% |
| 9 | Methyl trimethicone | 0.00% | 1.75% | 1.75% |
| 10 | VP/Eicosene copolymer | 1.00% | 1.00% | 1.00% |
| 11 | Cetearyl alcohol | 0.36% | 0.36% | 0.36% |
| | Total Oil Ingredients | 23.10% | 23.10% | 23.10% |
| | Emulsifiers | | | |
| 12 | Steareth-21 | 0.80% | 0.80% | 0.80% |
| 13 | Steareth-2 | 0.60% | 0.60% | 0.60% |
| 14 | Potassium cetyl phosphate & Hydrogenated palm glycerides | 3.00% | 3.00% | 3.00% |
| | Total Emulsifiers | 4.40% | 4.40% | 4.40% |
| X | Water Phase Ingredients | | | |
| 15 | Disodium EDTA | 0.10% | 0.10% | 0.10% |
| 16 | Glycerin | 4.00% | 4.00% | 4.00% |
| 17 | Benzyl alcohol | 1.00% | 1.00% | 1.00% |
| 18 | Methylparaben | 0.10% | 0.10% | 0.10% |
| 19 | Propylparaben | 0.05% | 0.05% | 0.05% |
| 20 | Water | 62.25% | 62.25% | 62.25% |
| | Total Water Ingredients | 67.50% | 67.50% | 67.50% |
| | Other Ingredients | | | |
| 21 | Acrylamide/Sodium acryloyldimethyl taurate copolymer | 2.50% | 2.50% | 2.50% |
| 22 | Aluminum starch octenyl succinate | 2.50% | 2.50% | 2.50% |
| | Total Other Ingredients | 5.00% | 5.00% | 5.00% |
| | Total | 100.00% | 100.00% | 100.00% |

***On a molar basis, 4.5% C20 methoxycrylene is equal to 2.75% Octocrylene
PROCEDURE
1. Charge secondary vessel with 1-7. With stirring, heat to 90° C. Add in order 10-14. Continue stirring until homogeneous.
2. Charged primary vessel with water (20). With stirring, ad 15-16. Heat to 90° C.
3. Add oil phase (1-7, 10-14) to water phase (20, 15, 16). Stir vigorously for 10 minutes. Switch to homomixer and homogenize until temperature is below 55
4. When temperature of emulsion is below 55° C., switch to sweep stirring. Preblend 17-19. Add to emulsion when temperature is below 45° C.
5. Add 21 and continue sweep stirring as emulsion thickens. When smooth, add 22. Pre-blend 8 and 9 and add to batch.
6. Q.S. water and package when temperature of batch is less than 35° C.

The surprising photostability of the sunscreen compositions of Table I, including methoxy crylene, in comparison to the octocrylene of the prior art, is shown in FIG. 1, which is a graph of the data of Examples 1 through 3, above, and in the following SPF reports for Examples 4-6.

TABLE 2

| | Example 4 (7% Ethylhexyl methoxycrylene) | Example 5 (0% Ethylhexyl methoxycrylene) | Example 6 8.8% Octocrylene) |
|---|---|---|---|
| Results of Irradiation with 35 MED | | | |
| Loss of UVA protection** | −18.26% | −80.47% | −55.96% |
| Loss of UVB protection** | −6.46% | −52.01% | −4.51% |
| Loss of SPF** | −7.43% | −70.42% | −16.00% |

TABLE 2-continued

\*\*Reported as Coefficients of Variation on report generated by Labsphere instrument software.

COMPOSITIONS OF FORMULATIONS TESTED FOR PHOTOSTABILITY

| # | Ingredients | CAB6-057 (7% Ethylhexyl methoxycrylene) | CAB6-058 (0% Ethylhexyl methoxycrylene) | CAB6-060 (0% Ethylhexyl methoxycrylene) |
|---|---|---|---|---|
| | Oil Phase Ingredients | | | |
| 1 | Avobenzone | 2.00% | 2.00% | 2.00% |
| 2 | Octyl methoxycinnamate (OMC) | 5.00% | 5.00% | 5.00% |
| 3 | Phenylethyl benzoate | 7.50% | 7.50% | 7.50% |
| 4 | Benzophenone-3 | 0.49% | 0.49% | 0.49% |
| 5 | Octocrylene | 1.80% | 1.80% | 8.80% |
| 6 | Ethylhexyl methoxycrylene\*\*\* | 7.00% | 0.00% | 0.00% |
| 7 | Polyisobutene | 0.00% | 7.00% | 0.00% |
| | Total Oil Ingredients | 23.79% | 23.79% | 23.79% |
| | Emulsifier | | | |
| 8 | Acrylates/C10-30 alkyl acrylate crosspolymer | 0.25% | 0.25% | 0.25% |
| 9 | Sorbitan laurate | 0.20% | 0.20% | 0.20% |
| | Total Emulsifiers | 0.45% | 0.45% | 0.45% |
| X | Water Phase Ingredients | | | |
| 10 | Disodium EDTA | 0.10% | 0.10% | 0.10% |
| 11 | Cetyl hydroxyethylcellulose | 0.30% | 0.30% | 0.30% |
| 12 | Glycerin | 4.00% | 4.00% | 4.00% |
| 13 | Benzyl alcohol | 1.00% | 1.00% | 1.00% |
| 14 | Methylparaben | 0.10% | 0.10% | 0.10% |
| 15 | Propylparaben | 0.05% | 0.05% | 0.05% |
| 16 | Triethanolamine | 0.40% | 0.40% | 0.40% |
| 17 | Water | 69.81% | 69.81% | 69.81% |
| | Total Water Ingredients | 75.76% | 75.76% | 75.76% |
| | Total | 100.00% | 100.00% | 100.00% |

PROCEDURE

1. Charge primary vessel with water (16). Dissolve 10. Heat to 85 degrees C. Disperse 11. Remove from heat. Continue stirring until 11 is fully dissolved.
2. In secondary vessel, add 2-7 and 9 with stirring. Add 1 and heat to 45 degrees C. Continue stirring until solution is clear.
3. Add 8 to oil and stir until completely incorporated.
4. When oil phase and water phase are 45 degrees C, add oil (1-7, 8, 9) to water (17, 10, 11). Maintain temperature and stir for 30 minutes.
5. Remove batch from heat. Preblend 12 and 16. Add to batch with stirring. Increase agitation as batch thickens.
6. Preblend 13-15, making sure that 14 and 15 are completely dissolved. Add to batch. Q.S. water and package when temperature of batch is less than 35° C.

Additional methoxy crylene molecules were tested in accordance with the procedure indicated in Table 2, wherein radical $R_3$ of the methoxy crylene of formula (I) has an $R_3$=ethyl hexyl (formula V):

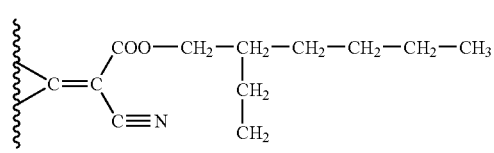

(V)

Figure 2:
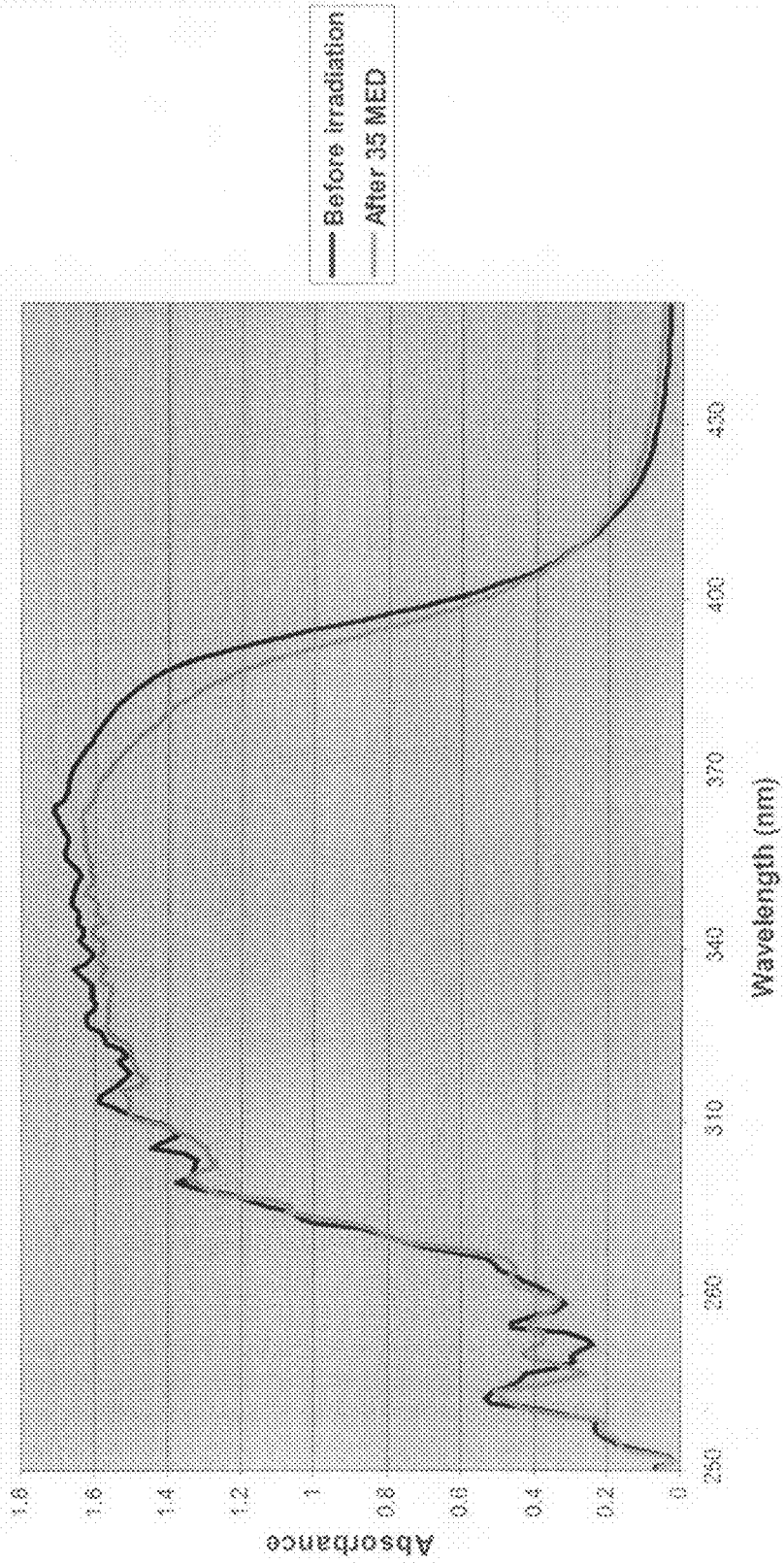
FIG. 2 is a graph showing to photostability of the sunscreen composition of Example 4 before and after irradiation with 35 MED of UV radiation.
Figure 3:
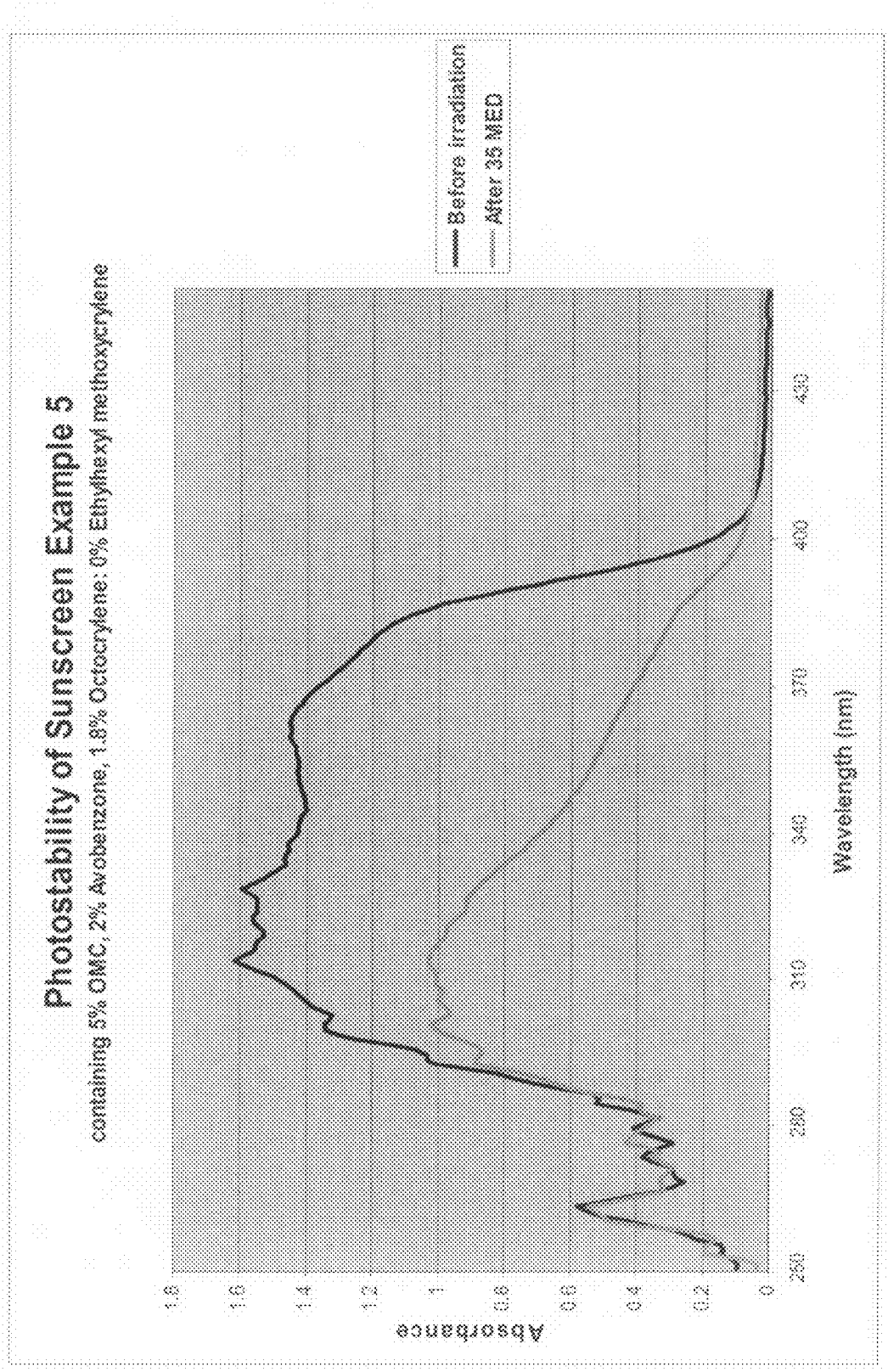
FIG. 3 is a graph showing to photostability of the sunscreen composition of Example 5 before and after irradiation with 35 MED of UV radiation.
Figure 4:
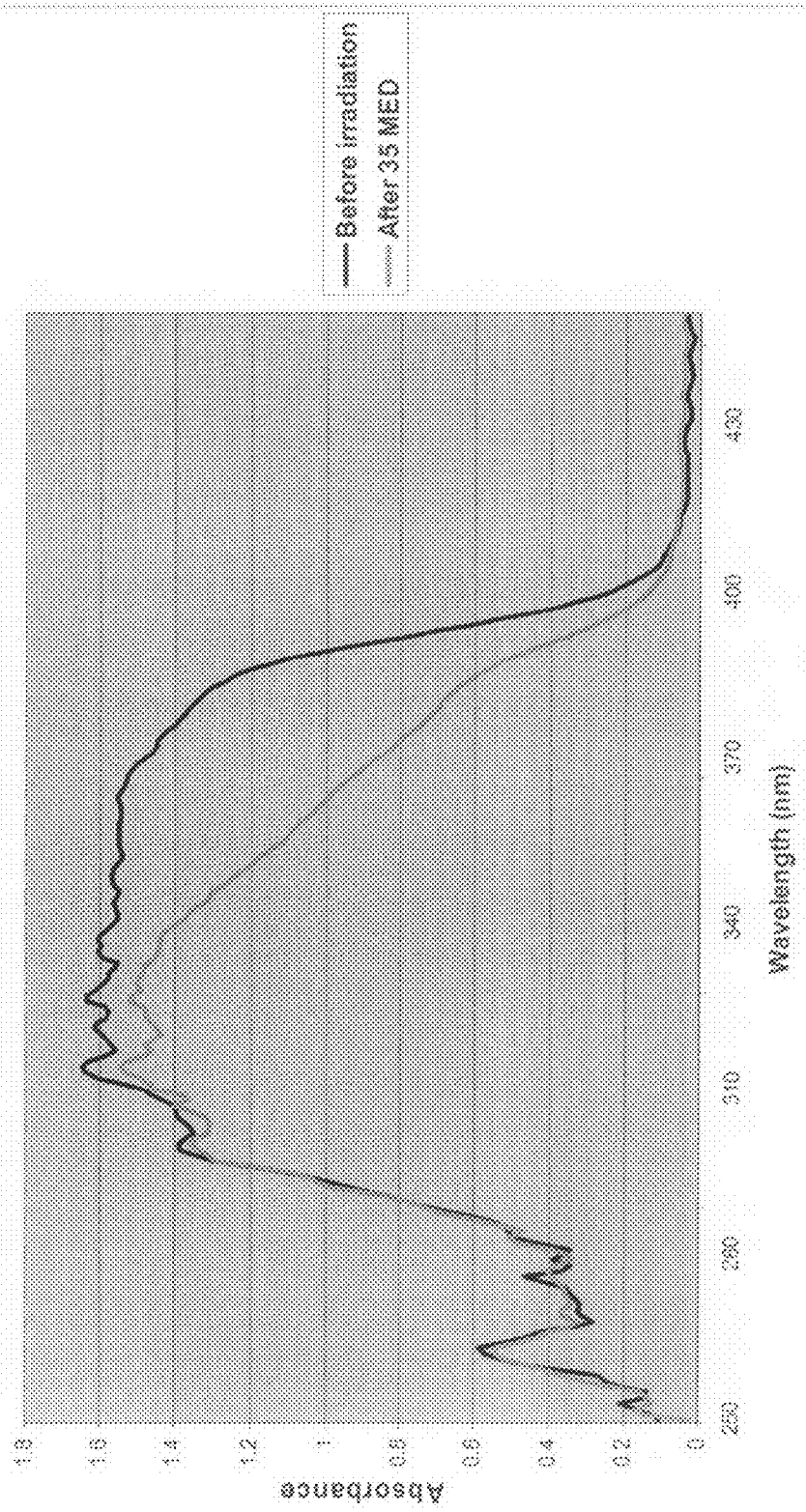
FIG. 4 is a graph showing to photostability of the sunscreen composition of Example 6 before and after irradiation with 35 MED of UV radiation.

The data for the sunscreen composition of Example 4 is shown in the graph of FIG. 2 and the data for the composition of Example 5 is shown in the graph of FIG. 3. For Examples 4-6, the data of Example 6 (shown in graph form as FIG. 4) compares 7% ethylhexyl methoxy crylene (formula V) and 1.8% octocrylene (Example 4) to 8.8% octocrylene with no alkoxy crylene. As shown in the graph of FIG. 4 and the following SPF reports for Examples 4-6, the alkoxy crylenes described herein are unexpectedly better photostabilizers than octocrylene.

| SPF REPORT | | | | |
|---|---|---|---|---|
| Sample: | Example 4 UV Photostability | | | |
| Comment: | 0, 35 MED | | | |
| Wavelength Range: | 290-400 nm | | | |
| Units: | | SPF | T(UVA) | T(UVB) |
| # of Scans: | | 2 | 2 | 2 |
| Mean: | | 24.67 | 4.52% | 5.43% |

| -continued | | | |
|---|---|---|---|
| SPF REPORT | | | |
| STD: | 1.83 | 0.83% | 0.35% |
| COV: | 7.43% | 18.26% | 6.46% |
| UVA/UVB Ratio: | 1.1 | | |
| Boots Star Rating: | N/A less than 5 Scans | | |
| Scan # | SPF | Critical Wavelength | |
| 1 | 25.97 | 385 | |
| 2 | 23.37 | 384 | |

| SPF REPORT | | | |
|---|---|---|---|
| Sample: | Example 5 UV Photostability | | |
| Comment: | 0, 35 MED | | |
| Wavelength Range: | 290-400 nm | | |
| Units: | SPF | T(UVA) | T(UVB) |
| # of Scans: | 2 | 2 | 2 |
| Mean: | 16.76 | 23.10% | 8.07% |
| STD: | 11.8 | 18.59% | 4.20% |
| COV: | 70.42% | 80.47% | 52.01% |
| UVA/UVB Ratio: | 0.72 | | |
| Boots Star Rating: | N/A less than 5 Scans | | |
| Scan # | SPF | Critical Wavelength | |
| 1 | 25.11 | 380 | |
| 2 | 8.41 | 372 | |

| SPF REPORT | | | |
|---|---|---|---|
| Sample: | Example 6 UV Photostability | | |
| Comment: | 0, 35 MED | | |
| Wavelength Range: | 290-400 nm | | |
| Units: | SPF | T(UVA) | T(UVB) |
| # of Scans: | 2 | 2 | 2 |
| Mean: | 23.83 | 11.80% | 5.27% |
| STD: | 3.81 | 6.61% | 0.24% |
| COV: | 16.00% | 55.96% | 4.51% |
| UVA/UVB Ratio: | 0.88 | | |
| Boots Star Rating: | N/A less than 5 Scans | | |
| Scan # | SPF | Critical Wavelength | |
| 1 | 26.52 | 382 | |
| 2 | 21.13 | 375 | |

In addition to the simple ester alkoxy crylene compounds of formula (I)-(V), the alkoxy crylene moieties can be attached as one or more terminal moieties on a polyester molecule, such as the alkoxy derivatives of the Di (NPG Crylene) Fumerate polyesters disclosed in this assignee's U.S. Pat. No. 7,235,587 ('587), hereby incorporated by references, as shown in formula (VI):

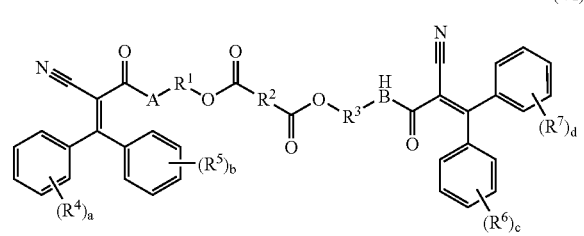

(VI)

wherein A and B are the same or different and are selected from the group consisting of oxygen, amino and sulfur; $R^1$ and $R^3$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$ is selected from the group consisting of $C_1$-$C_{30}$ alkyl, $C_2$-$C_{30}$ alkylene, $C_2$$C_{30}$ alkyne, $C_3$-$C_8$ cycloalkyl, $C_1$-$C_{30}$ substituted alkyl, $C_3$-$C_8$ substituted cycloalkyl, $C_1$-$C_{30}$ substituted alkylene, $C_2$-$C_{30}$ substituted alkyne; $R^4$, $R^5$, $R^6$ and $R^7$ are the same or different and are selected from the group consisting of $C_1$-$C_{30}$ alkoxy straight chain on branched, and a, b, c and d are each either 0 or 1, and a, b, c and d add up to 1, 2, 3, or 4.

The invention claimed is:
1. A method of photostabilizing a photon excited photoactive compound that reaches a singlet excited state when exposed to UV radiation in a sunscreen composition by accepting electronic singlet excited state energy from said photon-excited photoactive compound in said composition to quench the singlet excited state energy from the photon-excited photoactive compound and transfer the singlet excited state energy from the photon-excited photoactive compound to the compound of formula (I) thereby returning the photon-excited photoactive compound to its ground state so that the photon-excited photoactive compound can absorb more photons from UV radiation light before it undergoes a photochemical reaction destructive to its UV-absorbing capability, thereby photostabilizing said photoactive compound, comprising mixing said photoactive compound with a compound of formula (I):

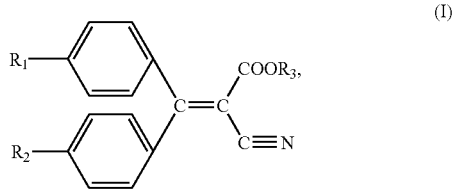

wherein one of $R_1$ and $R_2$ is a straight or branched chain $C_1$-$C_{12}$ alkoxy radical, and the non-alkoxy $R_1$ or $R_2$ is hydrogen and $R_3$ is a straight or branched chain $C_1$-$C_{24}$ alkyl radical, and exposing the mixture to UV radiation in an amount sufficient for the photoactive compound to reach an electronic singlet excited state, whereby the compound of formula (I) accepts the singlet excited state energy from the excited photoactive compound, thereby returning the photoactive compound to its ground state so that it is capable of absorbing additional UV radiation.

2. The method of claim 1, wherein $R_1$ is methoxy and $R_2$ is hydrogen.

3. The method of claim 1, wherein $R_2$ is methoxy and $R_1$ is hydrogen.

4. The method of claim 3, wherein $R_3$ is a $C_{12}$-$C_{24}$ straight chain or branched alkyl.

5. The method of claim 1, wherein the compound of formula (I) is present in an amount in the weight range of 0.1% to 20%, based on the total weight of the composition.

6. The method of claim 1, wherein the compound of formula (I) is present in an amount in this weight range of 0.1% to 10%, based on the total weight of the composition.

7. The method of claim 6, wherein the compound of formula (I) is present in an amount in the weight range of 3% to 8%, based on the total weight of the composition.

8. The method of claim 1, wherein the compound of formula (I) is present in an amount in this weight range of 0.1% to 5%, based on the total weight of the composition.

9. The method of claim 1, wherein the molar ratio of the compound of formula (I) to the photoactive compound is less than 0.8.

10. The method of claim 1, wherein the molar ratio of the compound of formula (I) to the photoactive compound is about 0.1 to about 0.6.

11. The method of claim 1, wherein the photoactive compound is selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone; dibenzalacetone naptholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxyl-substituted benzophenone derivatives; methoxy-substituted benzophenone derivatives; uric acid derivatives; vilouric acid derivatives; tannic acid and derivatives thereof; hydroquinone; benzophenone derivatives; 1,3,5-triazine derivatives; phenyldibenzimidazole tetrasulfonate and salts and derivatives thereof; terephthalyidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; and combinations of the foregoing.

12. The method of claim 11, wherein the photoactive compound comprises a dibenzoylmethane derivative.

13. The method of claim 12, wherein the photoactive compound comprises a dibenzoylmethane derivative selected from the group consisting of 2-methyldibenzoylmethane; 4-methyldibenzoylmethane; 4-isopropyldibenzoylmethane; 4-tert-butyldibenzoylmethane; 2,4-dimethydibenzoylmethane; 2-5-dimethydibenzoylmethane; 4,4-diisopropyldibenzoylmethane; 4,4-dimethoxydibenzoylmethane; 4-tert-butyl-4-methoxdibenzoylmethane; 2-methyl-5-isopropy-4-methoxydibenzoylmethane; 2-methyl-5-tert-butyl-4-methoxydibenzoylmethane; 2,4-dimethyl-4-methoxydibenzoylmethane; 2,6-dimethyl-4-tert-butyl-4-methoxydibenzoylmethane, and combinations thereof.

14. The method of claim 11, wherein the photoactive compound comprises a derivative of cinnamic acid.

15. The method of claim 14, wherein the photoactive compound comprises 2-ethylhexyl-p-methoxycinnamate.

16. The method of claim 1, wherein the sunscreen composition further comprises a diester or polyester of naphthalene dicarboxylic acid selected from the group consisting of compounds of formula (II) and (III), and combinations thereof:

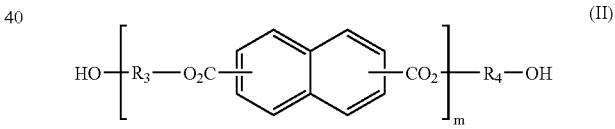

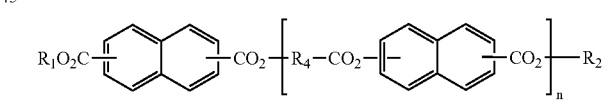

wherein $R_1$ and $R_2$ are the same or different and selected from the group consisting of $C_1$-$C_{22}$ alkyl groups, diols having the structure HO—$R_4$—OH, and polyglycols having the structure HO—$R_3$—(—O—$R_4$-)n-OH; wherein each $R_3$ and $R_4$ is the same or different and selected from the group consisting of $C_1$-$C_6$ straight or branched chain alkyl groups; and wherein m and n are each in a range of 1 to 100.

17. The method of claim 16, wherein the diester comprises a diester of formula (III) wherein $R_1$ and $R_2$ are 2-ethylhexane.

18. The method of claim 1, wherein said composition includes a cosmetically acceptable carrier.

19. The method of claim 1, wherein said composition includes an oil phase having a dielectric constant of at least about 8.

* * * * *